(12) United States Patent
Chern et al.

(10) Patent No.: US 8,354,511 B2
(45) Date of Patent: Jan. 15, 2013

(54) METHOD FOR PURIFYING PROTEIN

(75) Inventors: Ming-Kai Chern, Taipei (TW); Wei-Jhy Shiah, Kaohsiung (TW); Jyun-Jie Chen, Taipei (TW); Tzung-You Tsai, Taoyuan County (TW); Hsin-Yin Lin, Miaoli county (TW); Chien-Wei Liu, Pingtung County (TW)

(73) Assignee: Tamkang University, Taipei (TW)

( * ) Notice: Subject to any disclaimer, the term of this patent is extended or adjusted under 35 U.S.C. 154(b) by 269 days.

(21) Appl. No.: 12/786,615

(22) Filed: May 25, 2010

(65) Prior Publication Data

US 2011/0129895 A1 Jun. 2, 2011

(30) Foreign Application Priority Data

Nov. 30, 2009 (TW) .............................. 98140745 A

(51) Int. Cl.
- *C12N 9/00* (2006.01)
- *C12N 9/02* (2006.01)
- *C12N 9/10* (2006.01)
- *A23J 1/00* (2006.01)

(52) U.S. Cl. ......... 530/416; 435/183; 435/189; 435/193

(58) Field of Classification Search ........................ None
See application file for complete search history.

(56) References Cited

OTHER PUBLICATIONS

Tamaki et al. Methods Enzymol. 1982;89 Pt D:469-73.*
Saint-Prix et al. Microbiology. Jul. 2004:150(Pt 7):2209-20.*
Accession AAT92896, Apr. 24, 2007.*
Giddings, J.C., Unified Separation Science, Wiley-Interscience, New York, 1991. pp. 16-36.
Haddad et al., J. Chromatogr., 1985, 318: 279-288.
Roberts et al., Anal. Chem., 1981, 53: 1691-1695.
Okada, T. and Kuwamoto, T., J. Chrormatogr., 1985, 350: 317-323.
J.R. Blackwell, R. Horgan, FEBS Lett., 1991, 295: 10-12.
J.C. Anderson, S.C. Peck, Plant J., 2008, 55: 881-885.
G.L. Peterson, Determination of total protein, in: C.H.W. Hirs, S.N. Timasheff (Eds.), Methods in Enzymology, vol. 91: Enzyme Structure, Academic Press, New York, 1983, pp. 95-119.

\* cited by examiner

*Primary Examiner* — Christian Fronda
(74) *Attorney, Agent, or Firm* — Stuart D. Frenkel; Frenkel & Associates, P.C.

(57) ABSTRACT

A method is provided for purifying protein having steps of loading a sample containing proteins into a column containing an ion exchanger in a first direction to allow the ion exchanger to absorb proteins; and passing a salt solution through the column in a second direction opposite to the first direction to elute a target protein from the ion exchanger. The method is proven as capable of improving homogeneity of eluted target protein without combining minute and complicated techniques for protein purification. Therefore, the method is convenient, efficient and economic for purifying proteins.

14 Claims, 5 Drawing Sheets

METHOD FOR PURIFYING PROTEIN

BACKGROUND OF THE INVENTION

1. Field of the Invention

The invention relates to a method of protein purification, particularly to a method for purifying protein by chromatography.

2. Description of the Prior Arts

Ion exchange chromatography is one of the most common procedures for protein purification. Conventional ion exchange chromatography includes loading a protein sample in a direction to a column packed with ion exchanger to allow charged groups on proteins to interact with immobilized groups on the ion exchanger, whereby proteins can be absorbed by the ion exchanger, which is usually described as an equilibrium model (Giddings, J. C., *Unified Separation Science*, Wiley-Interscience, New York, 1991. pp. 16-36). Subsequently, a gradient of salt solution is introduced into the column from the same direction as the protein sample, whereby proteins binding to the ion exchanger to different extents are respectively eluted at different salt concentrations. However, ion exchange chromatography lacks a specific affinity. Therefore, separating a target protein from undesired impurity by conventional ion exchange chromatography usually requires further purification, such as affinity chromatography or preparation of specific antibodies, which dramatically elevates cost of protein purification.

In analytical chemistry, a method called "back flush" has been developed to better separate inorganic ionic species on ion exchangers. By simply reversing the flow direction of elution relative to that of sample loading, this method is aimed to minimize peak spreading (Haddad et al., *J. Chromatogr.*, 1985, 318: 279-288), avoid problems of irreversible ion exchange (Roberts et al., *Anal. Chem.*, 1981, 53: 1691-1695) and reduce the dip peak (Okada, T. and Kuwamoto, T., *J. Chrormatogr.*, 1985, 350: 317-323). Specifically, by loading the sample into the column in the opposite direction to that in which the target ion is eluted, the band broadening is minimized in the concentrator column through compression of the sample ions into a compact band during the initial stages of elution from the concentrator column (Haddad et al., supra). Because the direction of process can affect the result of separation, not only equilibrium interactions but also nonequilibrium interactions may play a role in this method.

Nevertheless, contrary to simple inorganic ions, proteins are large molecules consisting of multiple amino acids. Current techniques for purifying proteins suffer from band broadening and usually require further purification from elution fractions from a broad salt concentration range to obtain a homogenous protein. In the other words, there is still a need for obtaining a protein with higher homogeneity.

To overcome the shortcomings, the present invention provides a method for purifying protein to mitigate or obviate the aforementioned problems.

SUMMARY OF THE INVENTION

The main objective of the present invention is to provide a method for purifying protein, which can obtain a target protein with enhanced homogeneity in a single procedure without utilizing other means for purification, which results in reduction of trivial and complicated steps, such as adding extra affinity tags for specific recognition by genetic engineering technique.

Therefore, the present invention provides a method for purifying protein, comprising steps of:

loading a sample containing proteins into a column containing an ion exchanger in a first direction to allow the ion exchanger to absorb proteins; and passing a salt solution through the column in a second direction opposite to the first direction to elute a target protein from the ion exchanger.

Preferably, the step of passing a salt solution through the column in a second direction opposite to the first direction to elute a target protein from the ion exchanger includes:

passing a gradient of salt solution through the column in the second direction to obtain multiple eluted fractions; and determining and collecting a part of the multiple eluted fractions containing the target protein to obtain the target protein.

The method in accordance with the present invention comprises: selecting a working pH value higher than pI value of a target protein; loading a sample containing proteins into a column in a direction; and eluting the column in a reverse direction, whereby an eluate containing the target protein with homogeneity is obtained. The method in accordance with the present invention requires no further purification of the eluted fractions by affinity columns to obtain a homogenous target protein. Based on the aforesaid, the present invention provides a method for conveniently, efficiently and effectively purifying protein.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
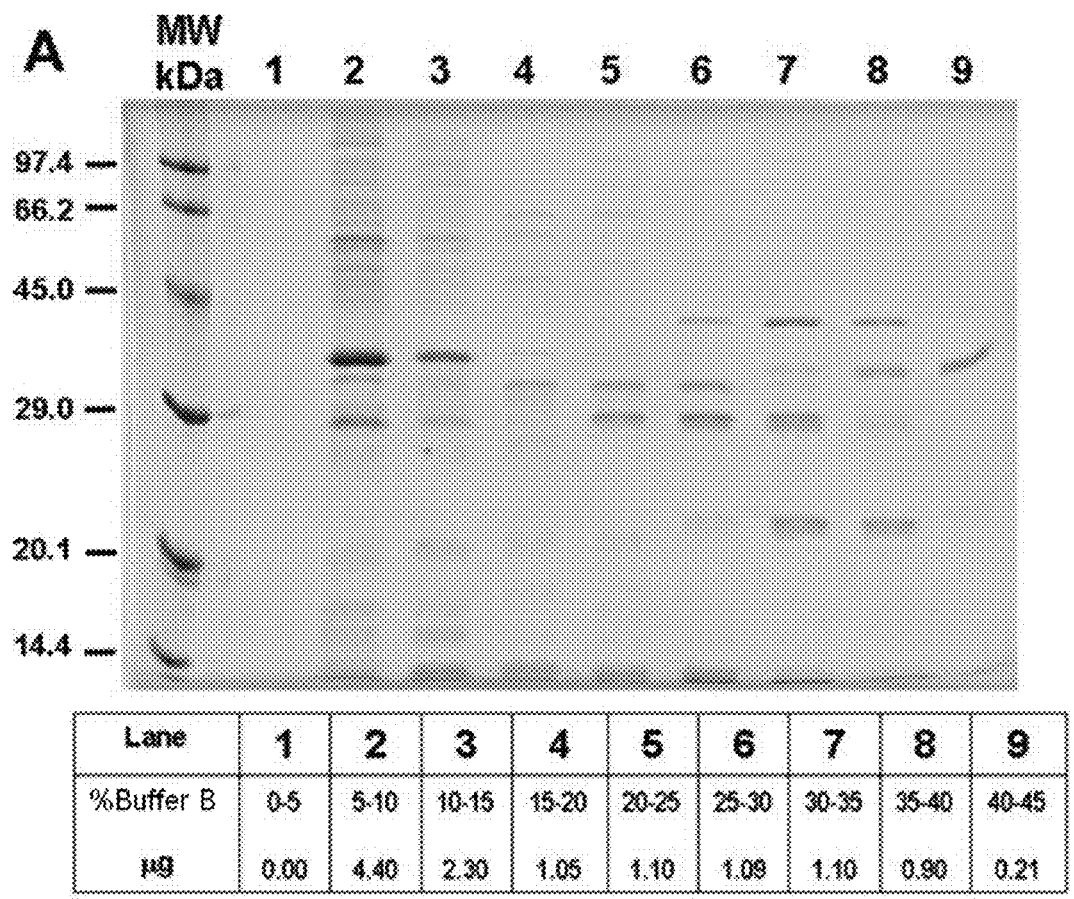
FIG. 1 illustrates results of SDS-PAGE analysis of fractions containing ALD4p, which are eluted with 0 to 45% Buffer B by conventional ion exchange chromatography.

The present invention provides a method for purifying protein based on ion exchange chromatography, particularly suitable for purification of over-expressed recombinant proteins.

A method for purifying protein in accordance with the present invention comprises steps of:

loading a sample containing proteins into a column containing an ion exchanger in a first direction to allow the ion exchanger to absorb proteins; and passing a salt solution through the column in a second direction opposite to the first direction to elute a target protein from the ion exchanger.

As known in the field of the art, said ion exchanger preferably is packed in a cylinder column. The column has two ends and two openings. The two openings are respectively formed at the two ends of the column. In a preferred embodiment, the column is vertically oriented and has upper and lower ends.

In a preferred embodiment of the present invention, the first direction is from an upper end to a lower end of the column, wherein the sample containing proteins is introduced into the column through an opening at the upper end and flows out through an opening at the lower end; and the second direction is from the lower end of the column to the upper end of the column, wherein the salt solution is introduced into the column through the opening at the lower end and flows out through the opening at the upper end.

In another preferred embodiment of the present invention, the first direction is from the lower end of the column to the upper end of the column, wherein the salt solution is introduced into the column through the opening at the lower end and flows out through the opening at the upper end; and the second direction is from the upper end of the column to the lower end of the column, wherein the sample containing proteins is introduced into the column through an opening at the upper end and flows out through an opening at the lower end.

According to the present invention, the sample containing proteins may be, but is not limited to: any cell extract that is essentially depleted of undesired lipids and nucleic acids, such as a supernatant obtained by centrifuging crude cell lysate.

According to the present invention, the term "elute", as used herein, refers to introducing a salt solution into a column with ion exchanger absorbing proteins, whereby a protein binding to the ion exchanger will be flushed out by ion exchange.

According to the present invention, the term "eluate", as used herein refers to a solution formed from a solvent in combination with its solute emerging from a column in an eluting step.

According to the present invention, the ion exchanger is ion exchange resin or ion exchange gel. In a preferred embodiment, the ion exchanger is anion exchanger.

In a preferred embodiment of the present invention, the anion exchanger may be, but is not limited to: gel, such as crosslinked, beaded-form of agarose, conjugated with a quaternary amine groups, manufactured under the tradename Q Sepharose™ by Amersham Biosciences. Q Sepharose™ comprises a substrate selected from Sepharoses™ with large pores suitable for chromatography at ambient temperature.

According to the present invention, the salt solution is introduced into the column in a second direction to elute ion exchanger absorbing proteins, wherein the salt solution has a pH value sufficient to elute the target protein from the ion exchanger at an initial gradient concentration, whereby the target protein is obtained.

The isoelectric point (pI) of the target protein in accordance to the present invention, especially for a recombinant protein with a known amino acid sequence, can be a theoretical pI value, which is used as a reference to select a preferred pH value in the method for purifying protein in accordance with the present invention, or as revealed in the two-dimensional polyacrylamide gel electrophoresis (2D-PAGE) profiles (such as documented in the SWISS-2DPAGE database).

The pI value of the target protein also can be an experimental pI value determined by isoelectric focusing analysis.

In a preferred embodiment in accordance with the present invention, the salt solution is at a pH value ranged from 1.5 to 2.5 unit higher than the pI value of the target protein.

According to the present invention, the step of passing a salt solution through the column in a second direction opposite to the first direction to elute a target protein from the ion exchanger includes:

passing a gradient of salt solution through the column in the second direction to obtain multiple eluted fractions; and determining and collecting a part of the multiple eluted fractions containing the target protein to obtain the target protein.

According to the present invention, the gradient of salt solution is formed by mixing two different salt solutions at high and low salt concentrations, wherein the gradient is formed by gradually increasing a ratio of the salt solution at the high salt concentration relative to the one at the low salt concentration.

According to the present invention, the step of determining and collecting a part of the multiple eluted fractions containing the target protein to obtain the target protein includes: respectively analyzing multiple eluted fractions by electrophoresis or any other protein analysis method to determine the part of the multiple eluted fractions containing the target protein. A concentration of the salt solution corresponding to one of the eluted fractions containing the target protein may be assigned as the salt concentration able to elute the target protein in accordance with the present invention.

In a preferred embodiment of the present invention, the target protein has a pI value ranging from 5.0 to 9.8.

According to the present invention, the target protein is selected from the group consisting of: aldehyde dehydrogenases (such as ALD4p and ALD6p) from *Saccharomyces* sp. and methyltransferase (such as Bud23p) from *Saccharomyces* sp.

In a preferred embodiment of the present invention, the target protein is aldehyde dehydrogenase; preferably, *Saccharomyces cerevisiae* ALD4p or ALD6p; and the salt solution in accordance with the present invention has a pH value ranging from 6.5 to 8.8.

In a preferred embodiment of the present invention, the target protein is methyltransferase; preferably, *Saccharomyces cerevisiae* Bud23p; and the salt solution in accordance with the present invention has a pH value ranging from 6.5 to 8.8.

The present invention was further illustrated by the following examples; it should be understood that the examples and embodiments described herein are for illustrative purposes only and should not be construed as limiting the embodiments set forth herein.

EXAMPLES

1. Materials and Methods (1) Pretreatment of Sources of the Proteins

DNA sequence corresponding to the mature length of mitochondrial ALD4p or the full-length open reading frame of ALD6 was cloned and inserted at the restriction sites NdeI/SpeI of pET 43.1c (Novagen) for protein expression. For expression of Bud23p, full-length open reading frame of Bud23 was cloned and inserted at the restriction sites NdeI/BamHI of pET 28c (Novagen). The theoretical pI values for recombinant ALD4p (NCBI GeneID: 854556; SGD Systematic Name: YOR374W), ALD6p (NCBI: GeneID: 856044;

SGD Systematic Name: YPL061W), and Bud23p (NCBI GeneID: 850414; SGD Systematic Name: YCR047c; GeneBank AccNo: AY692877) were derived from *Saccharomyces* Gemome Database™ (SGD database) (National Human Genome Research Institute of US National Institutes of Health) or calculated by Protein Calculator v3.3® (Christopher Putnam, Scripps. Research Institute), as 6.07, 5.18, and 9.69, respectively.

All three proteins were expressed in *Escherichia coli* strain BL21 (DE3) (Novagen). Expression of ALD4p was induced at 30° C., whereas that of ALD6p was induced at 24° C. to reduce degradation. Expression of Bud23p was induced at 18° C. in the presence of 0.5 M sorbitol and 2.5 mM betaine hydrochloride to reduce inclusion body (J. R. Blackwell, R. Horgan, *FEBS Lett.*, 1991, 295: 10-12). For ALD4p and ALD6p, 200 ml of culture was used; for Bud23p, 50 ml was used.

The cell pellet was then resuspended in 1/20 culture volume of lysis buffer (50 mM Tris-Cl [pH 7.4] containing 1 mM ethylenediaminetetraacetic acid [EDTA], 6 mM 2-mercaptoethanol, 10% glycerol, and 1 mM phenylmethylsulfonyl fluoride [PMSF]) prechilled at 4° C. *E. coli* cells were broken on ice with a Branson sonicator Digital Sonifier 250 D equipped with a ⅛-inch microtip. Each 2-second cycle was composed of alternating 1-second pulse of 28% amplitude and 1-second blank continued for 1 minute. A total of 3 minutes of sonication was carried out with each minute separated by a 1-minute interval on ice. The cell lysate was cleared at 5000×g and 4° C. for 10 minutes.

(2) Protein Purification and Separation

For purification of ALD4p and ALD6p, the supernatant was then applied onto a Q Sepharose™ Fast Flow column (1.6 cm diameter, 30 ml bed volume, Amersham Biosciences) preequilibrated with Buffer A (50 mM Tris-HCl [pH 7.6] containing 1 mM EDTA, 6 mM 2-mercaptoethanol, and 10% glycerol). The column used has a plunger filter to hold the ion exchanger in place so that the sample could be loaded either conventionally from the top or in a reverse manner from the bottom by connecting the sample tubing to either the top or bottom inlet of the column, respectively. The reverse loading mode has been called back flush (Haddad et al., supra; Okada, T. and Kuwamoto, T., supra). For either loading mode, the column was then washed with Buffer A and subsequently eluted with a gradient from 0 to 100% of Buffer B (with Buffer A containing 1 M NaCl) in the top-down direction.

For purification of Bud23p, Buffer A was replaced with Buffer C (50 mM boric acid [pH 8.8], 0.05 M NaCl, 6 mM 2-mercaptoethanol, 1 mM EDTA, and 10% glycerol) and Buffer B replaced with Buffer D (with Buffer C containing 1 M NaCl). Both Buffers C and D were adjusted to pH 8.8. Otherwise, the purification was carried out in the same way as for ALD4p and ADL6p. Throughout purification, the flow rate of 50 ml/hour was used and at an ambient temperature of 20° C.

(3) Evaluation of Effect of the Protein Separation

Both the conventional and back-flush modes of sample loading for ALD4p were carried out and compared. The conventional mode of sample loading refers to the flow direction in which the elution was carried out with gradient of salt solution being the same as that of sample loading. The spread of proteins in the eluate was analyzed by sodium dodecyl sulfate-polyacrylamide gel electrophoresis (SDS-PAGE).

2. Results and Discussion

Figure 2:
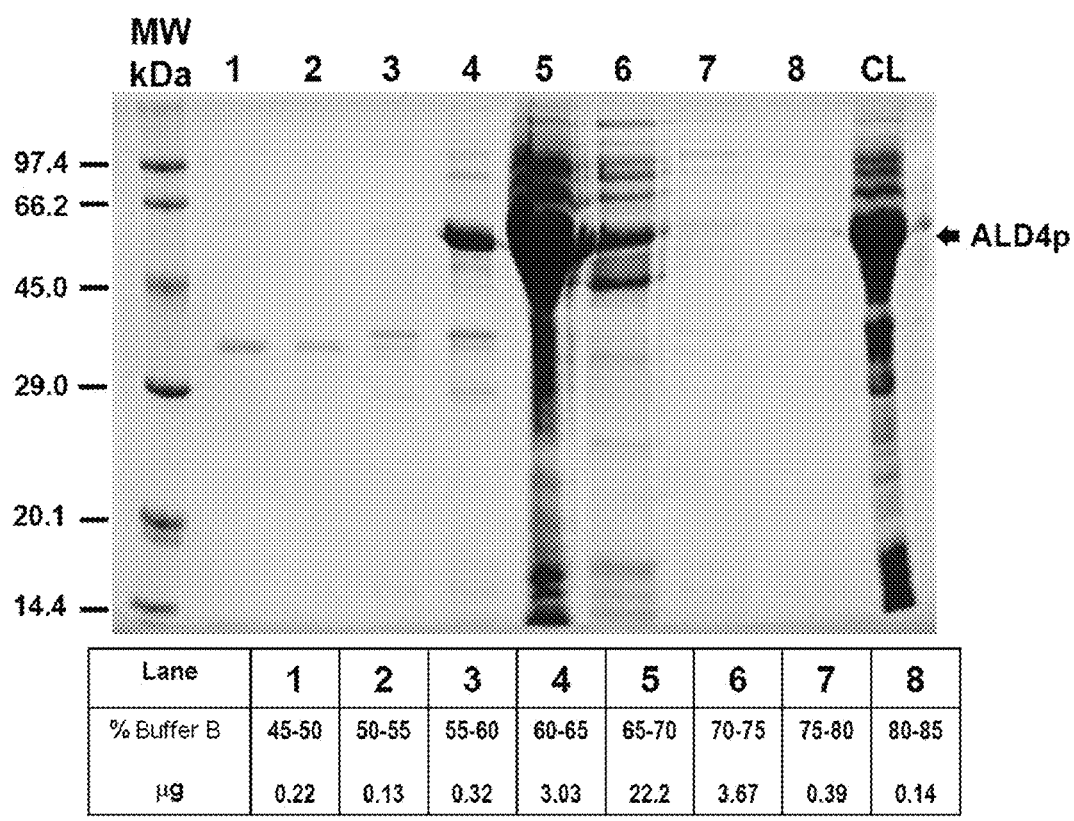
FIG. 2 illustrates results of SDS-PAGE analysis of fractions containing ALD4p, which are eluted with 45 to 50% Buffer B by conventional ion exchange chromatography.

With reference to FIGS. 1 and 2, Lanes 1 to 9, or Lanes 1 to 8 respectively represent fractions that were obtained by eluting with different ratio of Buffer B, wherein CL represented cleared lysate before purification, and MW represented molecular weight markers. The ALD4p band was indicated by an arrow. With the conventional mode, ALD4p was centered in fractions corresponding to 55 to 70% of Buffer B. Obviously, ALD4p in these fractions was mixed with a significant amount of impurities.

Figure 3:
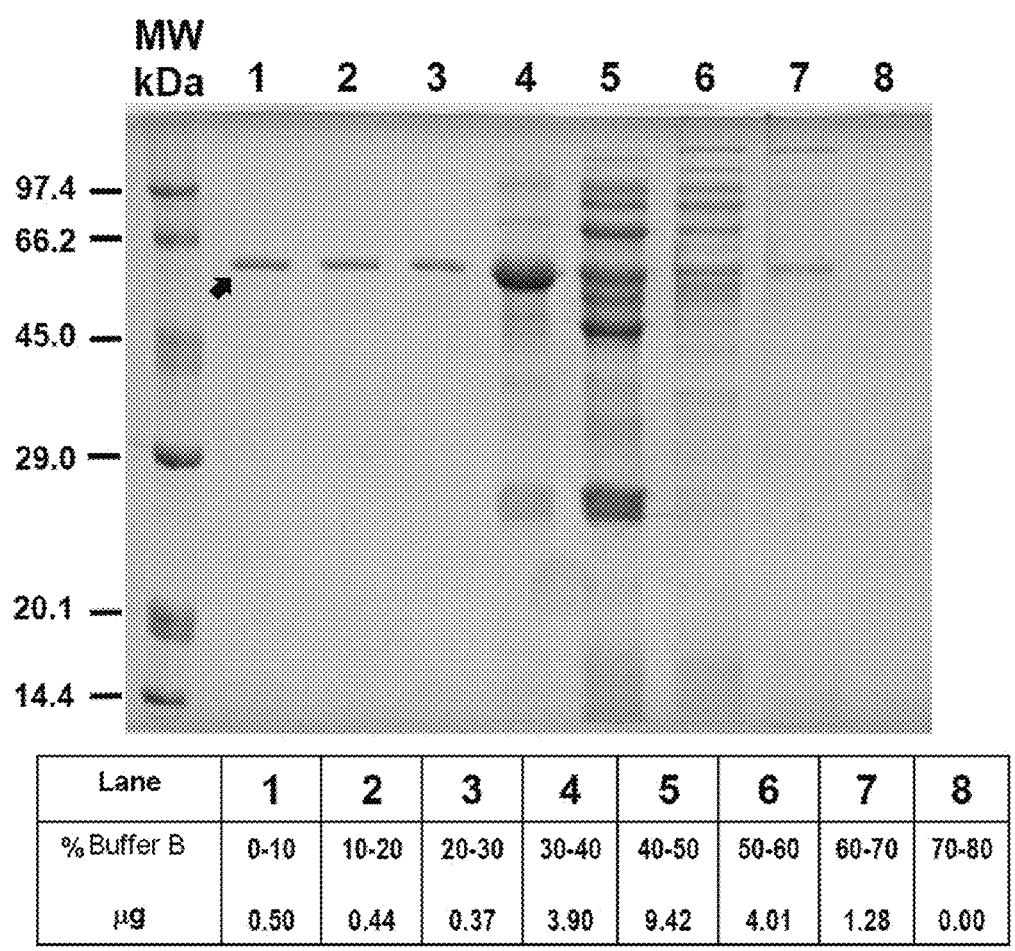
FIG. 3 illustrates results of SDS-PAGE analysis of fractions containing recombinant ALD4p obtained by the method in accordance with the present invention.

In contrast, with reference to FIG. 3, Lanes 1 to 8 respectively represent fractions that were obtained by eluting with different ratio of Buffer B, wherein CL represented cleared lysate before purification, and MW represented molecular weight markers. The ALD4p band was indicated by an arrow. With the back-flush mode, ALD4p turned out to be homogeneous as eluted in 0 to 30% of Buffer B. Thus, the applicants were able to accomplish single-step purification of the recombinant ALD4p on an anion exchanger by inverting the flow direction of sample loading and elution.

Figure 4:
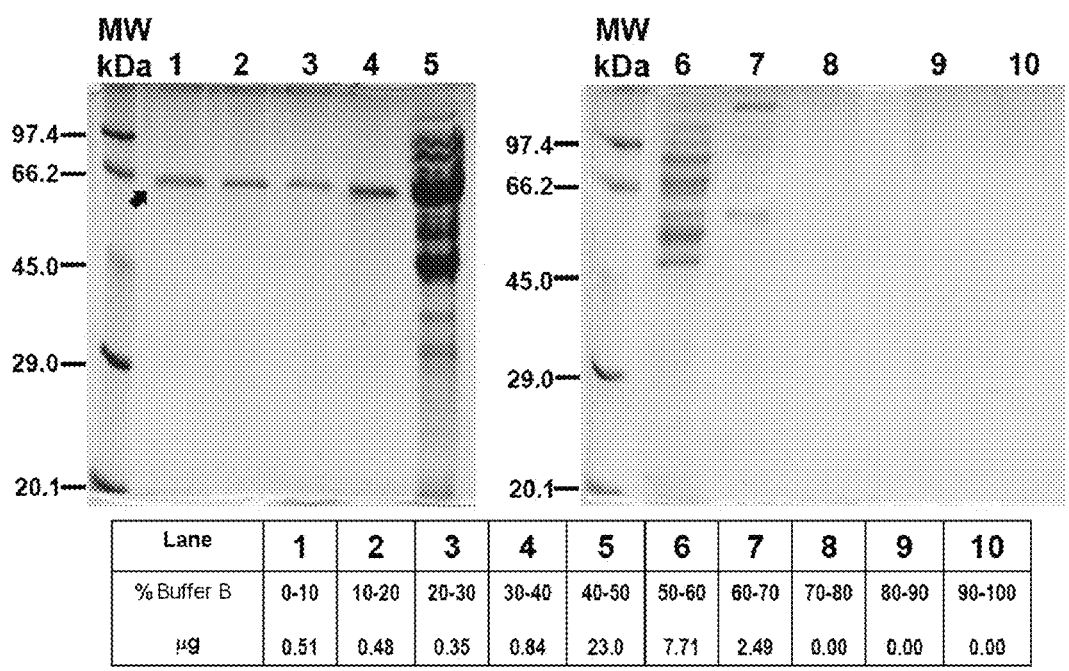
FIG. 4 illustrates results of SDS-PAGE analysis of fractions containing recombinant ALD6p obtained by the method in accordance with the present invention.

Similarly, ALD6p could also be separated to homogeneity by back flush in a single step. With reference to FIG. 4, Lanes 1 to 10 respectively represented fractions that were obtained by eluting with different ratio of Buffer B, wherein MW represented molecular markers. The ALD6p band was indicated by an arrow. The results indicated that homogeneous ALD6p was eluted in 0 to 40% of Buffer B.

The purification tables for ALD4p and ALD6p were compiled in Table 1. The total amount of the over-expressed protein for ALD4p and ALD6p was quantified by subtracting the amount of total protein extract of the uninduced cells from that of the corresponding over-expressing cells, where both kinds of cells are of the same culture volume, 200 ml, and the same growing condition. The total protein in the cellular extract was precipitated and redissolved in urea (J. C. Anderson, S. C. Peck, *Plant J.*, 2008, 55: 881-885) to eliminate the interference of nucleic acids in Bradford assay. The over-expressed protein obtained in this way was 13 mg for ALD4p and 18.5 mg for ALD6p.

TABLE 1

Purification of ALD4p and ALD6 by method in accordance with the present invention

|  | Total protein (mg) | Total activity (μmol/min) | Specific activity (μmol/min × mg) | Yield (%) | Purification fold |
| --- | --- | --- | --- | --- | --- |
| ALD4p | | | | | |
| Cleared lysate | 156 | 3.3 | 0.021 | 100 | 1 |
| Q Sepharose | 5.4 | 1.2 | 0.22 | 36 | 10.5 |

TABLE 1-continued

Purification of ALD4p and ALD6 by method in accordance with the present invention

|  | Total protein (mg) | Total activity (µmol/min) | Specific activity (µmol/min × mg) | Yield (%) | Purification fold |
|---|---|---|---|---|---|
| ALD6p | | | | | |
| Cleared lysate | 216 | 1575 | 7.3 | 100 | 1 |
| Q Sepharose | 3.5 | 214 | 6.1 | 14 | 8.4 |

Note.
The catalytic activity was determined at 22° C. with the following reaction mixtures: 0.6 mM propionaldehyde, 15 mM NADP$^+$, 100 mM KCl, and 100 mM sodium phosphate (pH 7.4) for ALD4p; 1 mM propionaldehyde, 3 mM NADP$^+$, 20 mM MgCl$_2$, and 100 mM sodium phosphate (pH 7.4) for ALD6p. The progress of reaction was followed spectrophotometrically by absorbance at 340 nm using 6.22 mM$^{-1}$ cm$^{-1}$ for NADPH. Protein concentration was determined by the microassay method of Bradford (G. L. Peterson, Determination of total protein, in: C. H. W. Hirs, S. N. Timasheff (Eds.), Methods in Enzymology, vol. 91: Enzyme Structure, Academic Press, New York, 1983, pp. 95-119).

Previously, the applicants managed to achieve one-step purification of recombinant Bud23p by engineering a His tag at the amino terminus. Unfortunately, the interaction between the tag and the chelating metal was too weak to recover pure Bud23p (data not shown), possibly due to a steric hindrance.

Because the pH condition (7.6) used for ALD4p and ALD6p was higher than their pI values (6.07 and 5.18, respectively), whereas Bud23p has a theoretical pI of 9.69 (much higher than 7.6), the applicants raised the pH of the buffer condition Bud23p. Buffers of pH 8.8 were employed for purification of Bud23p.

Figure 5:
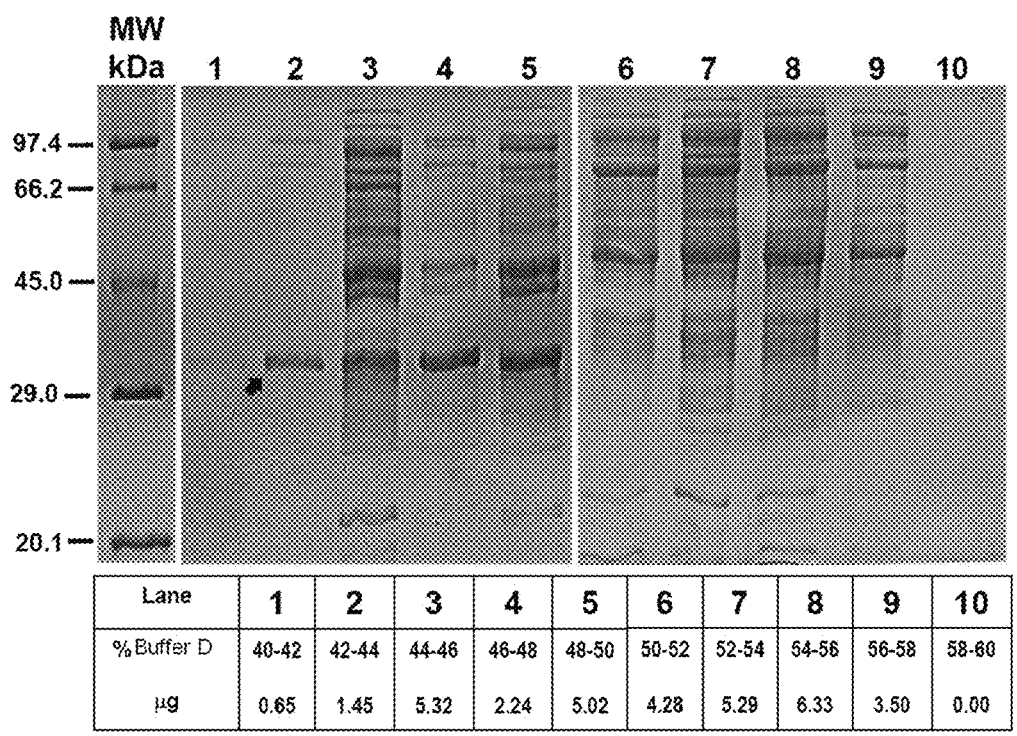
FIG. 5 illustrates results of SDS-PAGE analysis of fractions containing recombinant Bud23p obtained by the method in accordance with the present invention.

As shown in FIG. 5, Bud23p was indeed better separated from other impurities, particularly the fractions eluted in 40 to 44% of Buffer D. The front fractions in Buffer D lower than 40% almost did not contain any proteins according to SDS-PAGE analysis (not shown).

The applicants noticed that all of the purified fractions of the three recombinant proteins were eluted earlier than other impurities that were left behind in the back fractions, that is, in the higher salt concentration range of the gradient. It is shown that to achieve single-step purification by back flush on an anion exchanger with an increasing salt concentration gradient, wherein the pH conditions used should be higher than the pI values of the target proteins. This is supposed to hold back the impurities on the column to be eluted behind the target proteins.

To further reveal the effects of the buffer pH values on the applicability of this method, purification of ALD4p and ALD6p were also carried out in pH 6.0 (50 mM sodium phosphate, 0.05 M NaCl, 6 mM 2-mercaptoethanol, 1 mM EDTA, and 10% glycerol) and pH 8.8 (Buffer C) buffers. With pH 6.0 buffer, both proteins failed to bind to the column (not shown). In contrast, with pH 8.8 buffer, both proteins were retained so tenaciously in the column as to be eluted only along with contaminating proteins toward the high-salt range. Based on the pI values of ALD4p and ALD6p, a buffer 1.53 to 2.42 pH units higher than the pI value of the target protein may be recommended for the method for purifying protein in accordance with the present invention.

Based on the aforesaid, a method for purifying protein in accordance with the present invention is based on an ion exchange chromatography and can be performed by steps as follows: first, calculating the pI value of the recombinant protein of interest or determining the pI value experimentally by isoelectric focusing analysis second, selecting a working pH higher than the pI value; and third, loading the sample onto the column in the opposite direction to that in which it is eluted, and one can expect the homogeneous target protein to appear in the front fractions of elution.

Even though numerous characteristics and advantages of the present invention have been set forth in the foregoing description, together with details of the structure and features of the invention, the disclosure is illustrative only. Changes may be made in the details and arrangement of parts within the principles of the invention to the full extent indicated by the broad general meaning of the terms in which the appended claims are expressed.

What is claimed is:

1. A method for purifying protein, comprising:
   loading a sample containing proteins into a column containing an ion exchanger in a first direction to allow the ion exchanger to absorb proteins; and
   passing a salt solution through the column in a second direction opposite to the first direction to elute a target protein from the ion exchanger, wherein the salt solution has a pH value higher than the pI value of the target protein to elute the target protein from the ion exchanger.

2. The method of claim 1, wherein the step of passing a salt solution through the column in a second direction opposite to the first direction to elute a target protein from the ion exchanger includes:
   passing a gradient of salt solution through the column to obtain multiple eluted fractions; and
   determining and collecting a part of the multiple eluted fractions containing the target protein to obtain the target protein.

3. The method of claim 1, wherein the salt solution has a pH value ranging from 1.5 to 2.5 units higher than pI value of the target protein.

4. The method of claim 1, wherein the ion exchanger is ion exchange resin or ion exchange gel.

5. The method of claim 1, wherein the ion exchanger is anion exchanger.

6. The method of claim 1, wherein the ion exchanger is anion exchanger.

7. The method of claim 2, wherein the ion exchanger is anion exchanger.

8. The method of claim 5, wherein the target protein has a pI value ranging from 5.0 to 9.8.

9. The method of claim 8, wherein the target protein is aldehyde dehydrogenase.

10. The method of claim 9, wherein the aldehyde dehydrogenase is *Saccharomyces cerevisiae* ALD4p or ALD6p.

11. The method of claim 10, wherein the salt solution has a pH value ranging from 6.5 to 8.8.

12. The method of claim 8, wherein the target protein is methyltransferase.

13. The method of claim 12, wherein the methyltransferase is *Saccharomyces cerevisiae* Bud23p.

14. The method of claim 13, wherein the salt solution has a pH value ranging from 6.5 to 8.8.

* * * * *